(12) United States Patent
Inoue et al.

(10) Patent No.: US 10,318,441 B2
(45) Date of Patent: Jun. 11, 2019

(54) MODULAR MEASUREMENT APPARATUS

(71) Applicant: NGK Spark Plug Co., LTD., Nagoya (JP)

(72) Inventors: Yoshinori Inoue, Nagoya (JP); Katsunori Yazawa, Kasugai (JP); Hiroshi Inagaki, Komaki (JP); Wenjing Ma, Iwakura (JP); Kaoru Hisada, Obu (JP); Toshio Nakanishi, Niwa-gun (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 203 days.

(21) Appl. No.: 14/924,891

(22) Filed: Oct. 28, 2015

(65) Prior Publication Data

US 2016/0139098 A1    May 19, 2016

(30) Foreign Application Priority Data

Nov. 14, 2014  (JP) ................................. 2014-231750

(51) Int. Cl.
*G06F 13/00* (2006.01)
*G01N 33/00* (2006.01)
*G01D 11/24* (2006.01)

(52) U.S. Cl.
CPC ......... *G06F 13/00* (2013.01); *G01N 33/0031* (2013.01); *G01N 33/0037* (2013.01);
(Continued)

(58) Field of Classification Search
CPC ........... G01N 33/0031; G01N 33/0054; G01N 33/0037; G01N 33/0009; G01N 27/26; G01D 11/245
See application file for complete search history.

(56) References Cited

U.S. PATENT DOCUMENTS 5,746,976 A     5/1998  Yamada et al.
6,138,182 A *  10/2000  Hennessy ........... G06F 13/4068
                                                                710/16
(Continued)

FOREIGN PATENT DOCUMENTS

CN    102778537 A    11/2012
EP    2522961 A    11/2012
(Continued)

OTHER PUBLICATIONS

Extended European Search Repot dated Feb. 16, 2016 for the corresponding European Patent Application No. 15191365.4.
(Continued)

*Primary Examiner* — Ajay Ojha
(74) *Attorney, Agent, or Firm* — Leason Ellis LLP (57) ABSTRACT

A measurement apparatus includes a plurality of modules and a main unit for collecting measurement data output from the modules. The housing of the main unit can be carried by a user of the measurement apparatus, and the plurality of modules are removably accommodated in the housing. A controller area network interface circuit of the main unit collects the measurement data output from the modules accommodated in the housing. A main CPU of the main unit outputs the collected measurement data to, for example, a personal computer connected to the main unit. An internal memory and a USB memory connected to a USB memory module store the collected measurement data.

11 Claims, 6 Drawing Sheets

(52) U.S. Cl.
CPC ..... *G01N 33/0054* (2013.01); *G01N 33/0073* (2013.01); *G01D 11/245* (2013.01)

(56) References Cited

U.S. PATENT DOCUMENTS

| | | | |
|---|---|---|---|
| 6,148,656 | A | 11/2000 | Breton |
| 6,382,014 | B1 | 5/2002 | Breton |
| 6,470,732 | B1 | 10/2002 | Breton |
| 6,564,278 | B1 * | 5/2003 | Olson ................... G06F 13/409 710/300 |
| 2003/0074489 | A1 | 4/2003 | Steger et al. |
| 2004/0142602 | A1 | 7/2004 | Kamei et al. |
| 2005/0080550 | A1 * | 4/2005 | Nakamura ................ G01F 1/34 701/114 |
| 2005/0257605 | A1 * | 11/2005 | Colvin ...................... G01F 1/36 73/114.76 |
| 2006/0217881 | A1 * | 9/2006 | Pei ......................... G09B 29/10 701/432 |
| 2007/0245086 | A1 * | 10/2007 | Odom ................... G01D 9/005 711/115 |
| 2009/0153358 | A1 | 6/2009 | Park et al. |
| 2010/0105477 | A1 * | 4/2010 | Chang ...................... A63F 9/24 463/36 |
| 2010/0258329 | A1 | 10/2010 | Engelback et al. |
| 2012/0290268 | A1 | 11/2012 | Bey et al. |
| 2013/0136150 | A1 | 5/2013 | Haas et al. |
| 2014/0008094 | A1 | 1/2014 | Engelback et al. |

FOREIGN PATENT DOCUMENTS

| | | |
|---|---|---|
| JP | 49-053751 U | 5/1974 |
| JP | 58-132820 U | 9/1983 |
| JP | 05-081636 U | 11/1993 |
| JP | 08-170943 A | 7/1996 |
| JP | 09-257655 A | 10/1997 |
| JP | 11-108885 A | 4/1999 |
| JP | 2000-88711 A | 3/2000 |
| JP | 2002-116050 A | 4/2002 |
| JP | 2002-516981 A | 6/2002 |
| WO | WO-00/25108 A | 5/2000 |
| WO | WO-2007/102668 A | 9/2007 |
| WO | WO-2010/105268 A | 9/2010 |
| WO | WO-2011/140576 A | 11/2011 |

OTHER PUBLICATIONS

European Office Action dated Apr. 24, 2017 for the corresponding European Patent Application No. 15191365.4.

Extended European Search Report dated Feb. 16, 2016 for the corresponding European Application No. 15191365.4.

Mitrovics et al. "Modular Sensor Systems for Gas Sensing and Odor Monitoring: The MOSES Concept", *Accounts of Chemical Research*, Feb. 5, 1998, pp. 307-315, vol. 31, No. 5 , XP055247979.

Office Action dated Nov. 14, 2017 for the corresponding Japanese Patent Application No. 2014-231750.

Office Action dated Apr. 17, 2018 for the corresponding Chinese Patent Application No. 201510777486.4.

* cited by examiner

MODULAR MEASUREMENT APPARATUS

This application claims the benefit of Japanese Patent Applications No. 2014-231750, filed Nov. 14, 2014, which is incorporated herein by reference in its entity.

FIELD OF THE INVENTION

The present invention relates to a measurement apparatus which collects data from a plurality of sensors.

BACKGROUND OF THE INVENTION

Conventionally, there has been known a measurement apparatus which includes an NOx sensor and a data collection apparatus mounted on a vehicle so as to measure the concentration of NOx contained in exhaust gas discharged from an internal combustion engine in a state in which the vehicle is actually travelling on a road (see, for example, Japanese Patent Application Laid-Open (kokai) No 2000-88711).

Problems to be Solved by the Invention

A measurement apparatus which measures a plurality of gas components in addition to the concentration of NOx contained in exhaust gas and in which a function of collecting and processing data from a plurality of sensors is incorporated in advance has a problem in that when a trouble occurs in collection of data from one of the plurality of sensors, the entire measurement apparatus must be replaced for repair, which impairs the user-friendliness of the measurement apparatus.

The present invention has been accomplished in the view of such a problem, and its object is to improve the convenience of a measurement apparatus.

SUMMARY OF THE INVENTION

Means for Solving the Problems

The present invention accomplished so as to achieve the above-described object is a measurement apparatus which comprises a plurality of measurement modules which are connected to sensors in one-to-one relation and each of which includes at least a circuit configured to receive a sensor output from the corresponding sensor and outputting the received sensor output; and a main body portion which collects data output from the measurement modules.

The main body portion includes a housing and data collection unit. The housing can be carried by a user of the measurement apparatus, and the plurality of measurement modules are removably accommodated in the housing. The data collection unit collects the data output from the measurement modules accommodated in the housing.

Further, the main body portion includes at least one of output units and a storage section. The output unit outputs the collected data to an output destination device set in advance. The storage section stores the collected data.

The measurement apparatus of the present invention configured as described above collects data from the measurement modules after the measurement modules are installed in the housing. The measurement apparatus of the present invention performs at least one of an operation of outputting the collected data to the output destination device set in advance and an operation of storing the collected data. As a result, the measurement apparatus of the present invention allows the data from the measurement modules to be utilized at the output destination device or to be obtained from the storage section and be utilized.

The measurement apparatus of the present invention is configured such that the plurality of measurement modules can be removably accommodated in the housing. Therefore, the measurement apparatus of the present invention allows the user to collect desired data by installing a measurement module having a desired measurement function in the housing. Thus, the convenience of the measurement apparatus can be improved.

In the measurement apparatus of the present invention, when a trouble occurs in a measurement module installed in the housing, the measurement module having a trouble can be removed from the housing. Therefore, in the measurement apparatus of the present invention, when a trouble occurs in a measurement module, the trouble can be solved without replacing the entire measurement apparatus. Thus, the convenience of the measurement apparatus can be improved.

Further, since the measurement apparatus of the present invention is configured such that the housing for accommodating the measurement modules can be carried, the degree of freedom of the installation location of the measurement apparatus can be increased.

Also, the measurement apparatus of the present invention may comprise a plurality of connectors which are disposed within the housing and which are detachably connected to the measurement modules, wherein the plurality of connectors have the same shape and are arranged along an arrangement direction set in advance. As a result, the measurement apparatus of the present invention allows a plurality of measurement modules having the same measurement function to be attached to the main body portion of the measurement apparatus. Further, by making the connectors attached to the plurality of measurement modules have the same shape, it becomes possible to attach each measurement module to any of the plurality of connectors disposed within the housing. As a result, the measurement apparatus of the present invention can increase the degree of freedom of the installation position of the measurement module within the housing.

Also, in the measurement apparatus of the present invention, the plurality of connectors may be arranged along the arrangement direction at intervals equal to a shortest arrangement direction length set in advance to coincide with the length of the smallest measurement module along the arrangement direction. The smallest measurement module refers to a measurement module having the shortest length along the arrangement direction among the plurality of measurement modules. As a result, the measurement apparatus of the present invention allows the plurality of measurement modules to be attached to the main body portion along the arrangement direction at intervals equal to n times the smallest arrangement direction length, where n is an integer. Therefore, the measurement apparatus of the present invention allows the length of each measurement module along the arrangement direction to be freely set in accordance with the capacity of the housing; i.e., the number of measurement modules which can be accommodated in the housing.

In the measurement apparatus of the present invention, each measurement module may include connection detection unit for detecting one of the plurality of connectors which is connected to the measurement module. As a result, the measurement apparatus of the present invention can specify the location of the measurement module accommodated in the housing, the location being that within the housing.

In the measurement apparatus of the present invention, at least one of the plurality of measurement modules may use, as the sensor, a direct-insertion-type sensor which is directly inserted into an exhaust pipe of an internal combustion engine so as to detect the state of exhaust gas within the exhaust pipe. As a result, the measurement apparatus of the present invention can detect the state of exhaust gas without introducing the exhaust gas into the measurement modules.

In the measurement apparatus of the present invention, each sensor and the corresponding measurement module may be detachably connected together. As a result, in the measurement apparatus of the present invention, when a trouble occurs in the sensor, the trouble can be solved by replacing the sensor only without replacing both the sensor and the measurement module. Thus, the convenience of the measurement apparatus can be improved.

The measurement apparatus of the present invention may be configured such that the main body portion and the measurement modules can send and receive data therebetween. As a result, the measurement apparatus of the present invention can not only collect data from the measurement modules but also provide information to the measurement modules.

The measurement apparatus of the present invention may further comprise position information obtainment unit that obtains information for specifying the present position of the measurement apparatus. As a result, the measurement apparatus of the present invention can relate the present position of the measurement apparatus to the measurement results of the measurement modules.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

An embodiment of the present invention will now be described with reference to the drawings.

Figure 1:
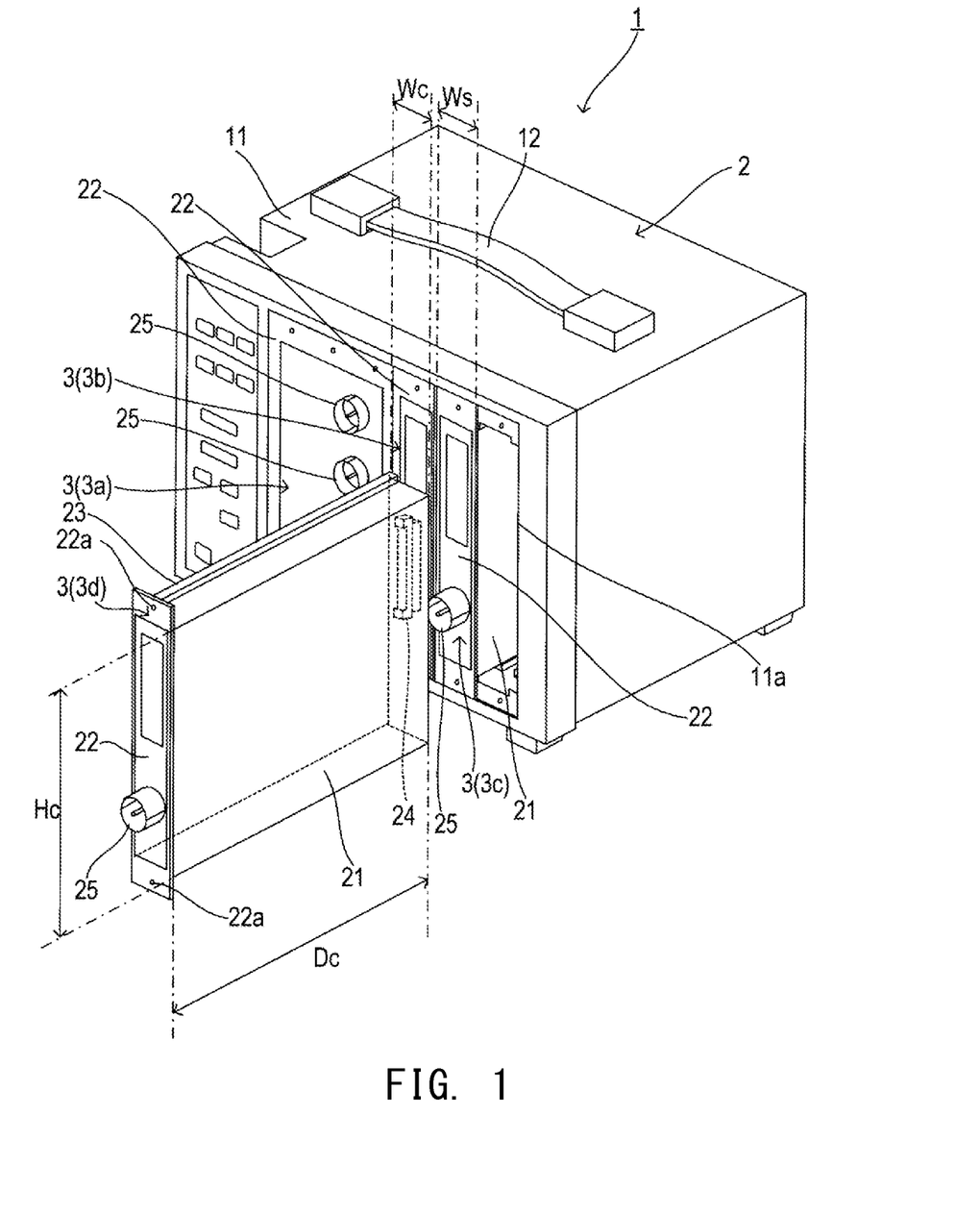
FIG. 1 is a perspective view of a measurement apparatus 1.

As shown in FIG. 1, a measurement apparatus 1 of an embodiment to which the present invention is applied includes one main unit 2 and four modules 3a, 3b, 3c, and 3d. In the following description, one module which represents the modules 3a, 3b, 3c, and 3d will be referred to as a "module 3."

The main unit 2 includes a housing 11 and a handle 12.

The housing 11 has a box-like shape of rectangular parallelepiped (in the present embodiment, for example, 30 cm (height)×40 cm (width)×30 cm (depth)) and accommodates the components of the main unit 2 and the module 3 therein.

A rectangular opening 11a is formed in the front surface among the six surfaces which constitute the rectangular parallelepiped of the housing 11. The module 3 is inserted through the opening 11a, whereby the module 3 is accommodated in the housing 11.

The handle 12 is attached to the top surface among the six surfaces which constitute the rectangular parallelepiped of the housing 11. A user of the main unit 2 can carry the main unit 2 by grasping the handle 12.

The module 3a is an apparatus into which a portion of exhaust gas discharged from a diesel engine is introduced and which measures the amount of particulate matters contained in the exhaust gas. The module 3b is an apparatus which measures the concentration of nitrogen oxides contained in the exhaust gas through use of an NOx sensor. The module 3c is an apparatus which measures the concentration of ammonia contained in the exhaust gas through use of an ammonia sensor. The module 3d is an apparatus which measures the air-fuel ratio of the exhaust gas through use of an air-fuel ratio sensor.

The module 3 includes a casing 21, a mounting plate 22, guide rails 23, a unit connection connector 24, and a sensor connection connector 25.

The casing 21 has a box-like shape of rectangular parallelepiped and accommodates the components of the module 3 therein.

The height Hc and depth Dc of the casing 21 are set in advance such that the modules 3a, 3b, 3c, and 3d have the same dimensions, so that the module 3a, 3b, 3c, and 3d are accommodated in the housing 11 in a state in which they are lined up in a horizontal direction.

The width Wc of the casing 21 is set such that the width Wc is approximately equal to n times a slot width Ws, which is the minimum unit of the width of the module 3, where n is an integer. Notably, the width Wc of the modules 3a is about three times the slot width. The widths Wc of the module 3b, 3c, and 3d are approximately equal to the slot width.

The mounting plate 22 is a rectangular plate member having a height approximately equal to the height of the rectangular opening 11a and a width approximately equal to the width Wc of the casing 21.

The mounting plate 22 is attached to the front surface among the six surfaces which constitute the rectangular parallelepiped of the casing 21. Notably, the mounting plate 22 is disposed such that the upper side among the four sides which constitute the rectangle of the mounting plate 22 is located above the upper side among the four sides which constitute the rectangle of the front surface of the casing 21. Further, the mounting plate 22 is disposed such that the lower side among the four sides which constitute the rectangle of the mounting plate 22 is located below the lower side among the four sides which constitute the rectangle of the front surface of the casing 21.

Through holes 22a are formed in portions of the mounting plate 22 which are not in contact with the casing 21. Screws for fixing the module 3 in a state in which it is accommodated in the main unit 2 are passed through the through holes 22a.

The guide rails 23 are attached to the top and bottom surfaces among the six surfaces which constitute the rectangular parallelepiped of the casing 21 (FIG. 1 does not show the guide rail 23 attached to the bottom surface). The guide rails 23 are provided such that they extend from the front surface toward the back surface, which surfaces constitute the rectangular parallelepiped of the casing 21, and they project from the top surface and the bottom surface, respectively.

The unit connection connector 24 is a connector for connecting the module 3 to the main unit 2 and is attached to the back surface of the casing 21. The unit connection connectors 24 of the modules 3a, 3b, 3c, and 3d have the same shape.

The sensor connection connector 25 is a connector for connecting a sensor to the module 3 and is attached to the front surface of the mounting plate 22.

Figure 2:
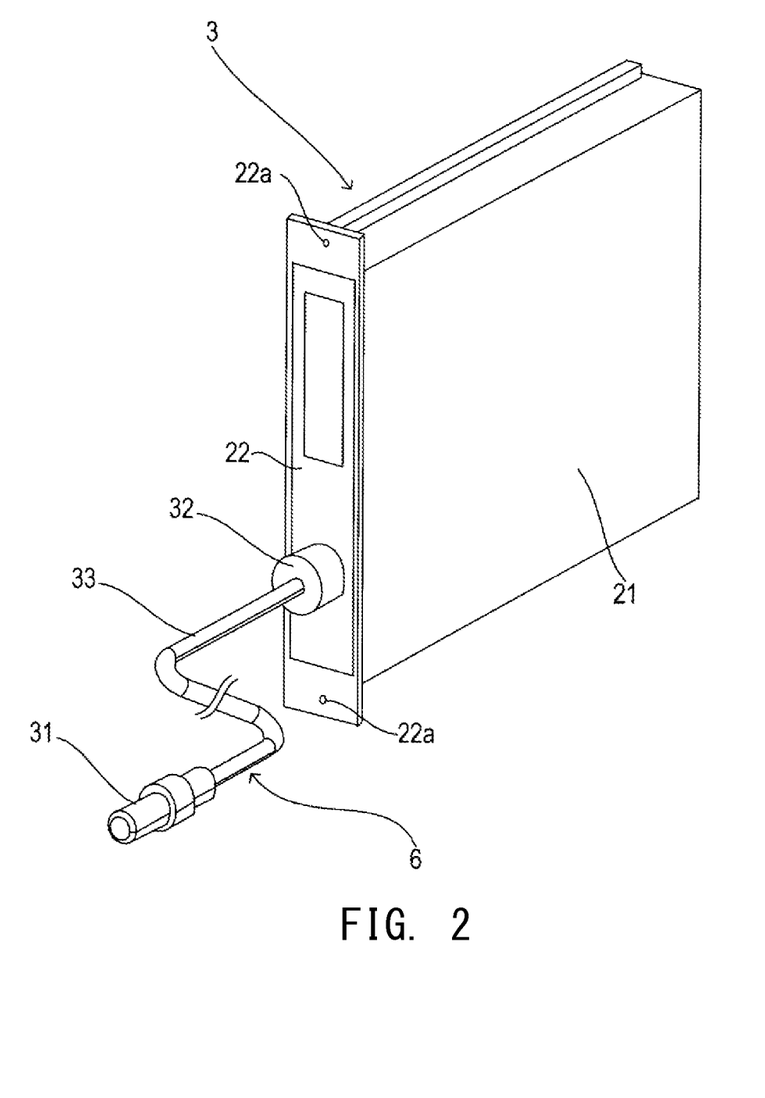
FIG. 2 is a perspective view of a module 3 and a sensor 6.

As shown in FIG. 2, a sensor 6 includes a sensor element 31, a connector 32, and a signal cable 33. The sensor element 31 detects a physical quantity corresponding to the function of the module 3 to which the sensor 6 is connected. The connector 32 has a structure which allows the connector 32 to be detachably mated with the sensor connection connector 25 of the module 3 to which the sensor 6 is connected. The signal cable 33 is a signal line for electrically connecting the sensor element 31 and the connector 32.

Therefore, as a result of the connector 32 of the sensor 6 and the sensor connection connector 25 of the module 3 being mated together, it becomes possible to input a detection signal from the sensor 6 into the module 3.

The sensors 6 connected to the modules 3b, 3c, and 3d are an NOx sensor, an ammonia sensor, and an air-fuel ratio sensor, respectively. Notably, each of the NOx sensor, the ammonia sensor, and the air-fuel ratio sensor is a direct-insertion-type sensor which is directly inserted into an exhaust pipe of an internal combustion engine.

Figure 3:
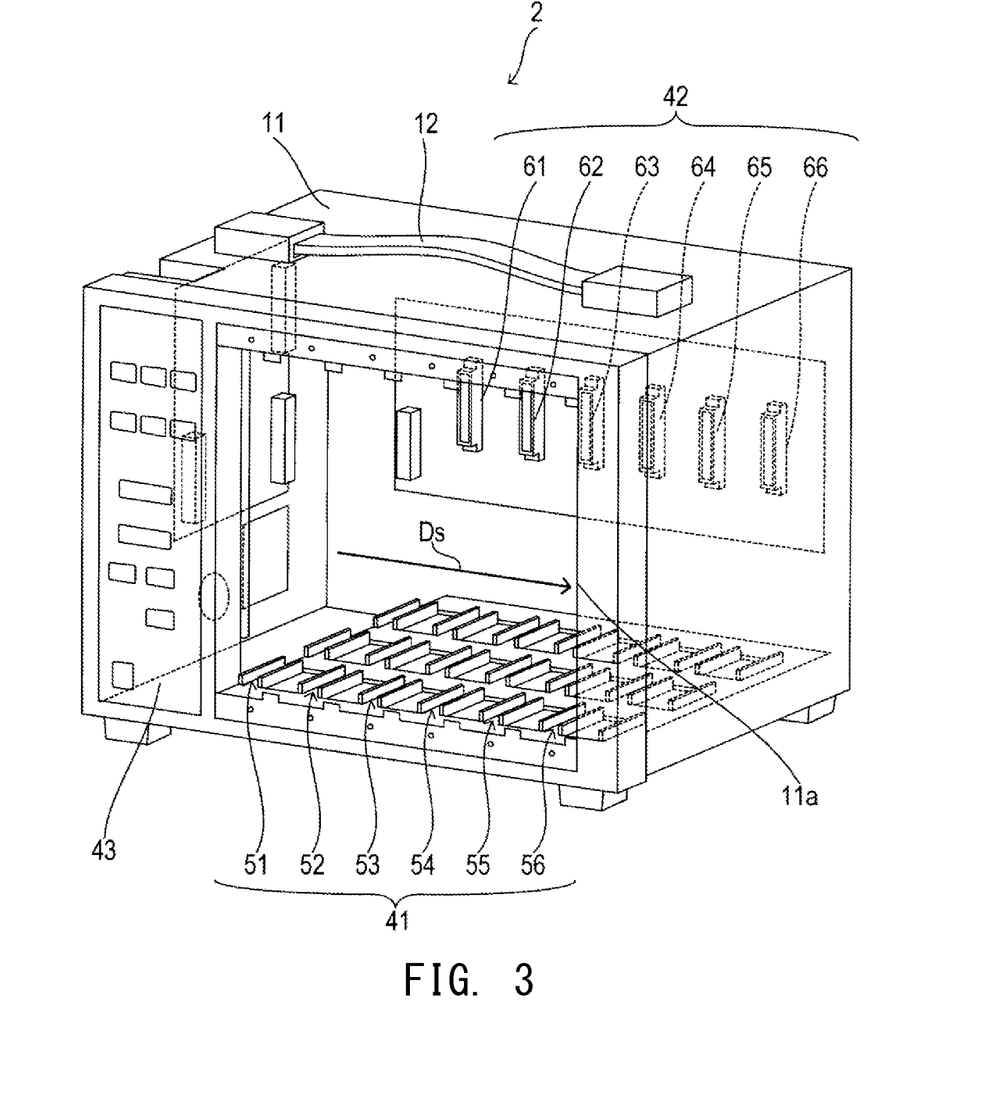
FIG. 3 is a perspective view of a main unit 2.

As shown in FIG. 3, the main unit 2 includes a slot guide groove group 41, a module connection connector group 42, and a switch panel 43.

The slot guide groove group 41 includes slot guide grooves 51, 52, 53, 54, 55, and 56 for six slots set in advance.

The slot guide grooves 51 to 56 are concave portions which can receive the guide rails 23 provided on the top and bottom surfaces of the casing 21 of the module 3. The slot guide grooves 51 to 56 are provided such that they extend from the front surface toward the back surface, which surfaces constitute the rectangular parallelepiped of the housing 11.

The slot guide grooves 51 to 56 are provided in the vicinity of each of the upper and lower sides of the rectangle of the rectangular opening 11a (FIG. 3 does not show the slot guide grooves 51 to 56 provided in the vicinity the upper side).

The slot guide grooves 51 to 56 are disposed at intervals equal to the slot width Ws along a slot arrangement direction Ds which is set in advance such that it becomes parallel to the upper and lower sides of the rectangle of the of the rectangular opening 11a.

Therefore, the module 3 can be accommodated in a slot corresponding to the slot guide grooves 51 by the following steps. First, when the module 3 located outside the housing 11 is inserted into the opening 11a, the guide rails 23 provided on the top and bottom surfaces of the casing 21 of the module 3 are fitted into the slot guide grooves 51 provided near the upper and lower sides of the opening 11a. Subsequently, in a state in which the guide rails 23 are fitted into the slot guide grooves 51, the module 3 is moved toward the interior of the housing 11 along the direction in which the slot guide grooves 51 extend. As a result, the module 3 is accommodated in the housing 11.

Notably, the modules 3 can be accommodated in slots corresponding to the slot guide grooves 52, 53, 54, 55, and 56 by the above-described steps. Hereinafter, the slots corresponding to the slot guide grooves 51, 52, 53, 54, 55, and 56 will be referred to as first, second, third, fourth, fifth, and sixth slots.

The module connection connector group 42 includes module connection connectors 61, 62, 63, 64, 65, and 66. The module connection connector 61, 62, 63, 64, 65, and 66 are connectors for connecting the modules 3 accommodated in the first, second, third, fourth, fifth, and sixth slots to the main unit 2.

The module connection connectors 61 to 66 are disposed at respective positions determined such that the module connection connectors 61 to 66 can be mated with the corresponding unit connection connectors 24 disposed on the back surfaces of the modules 3 when the modules 3 are accommodated in the first to sixth slots.

The switch panel 43 includes a plurality of switches for instructing operations of the main unit 2 and a plurality of LED (Light Emitting Diode) lamps for showing the operation state of the main unit 2. The switch panel 43 is disposed on the front surface among the six surfaces of the rectangular parallelepiped of the housing 11.

Figure 4:
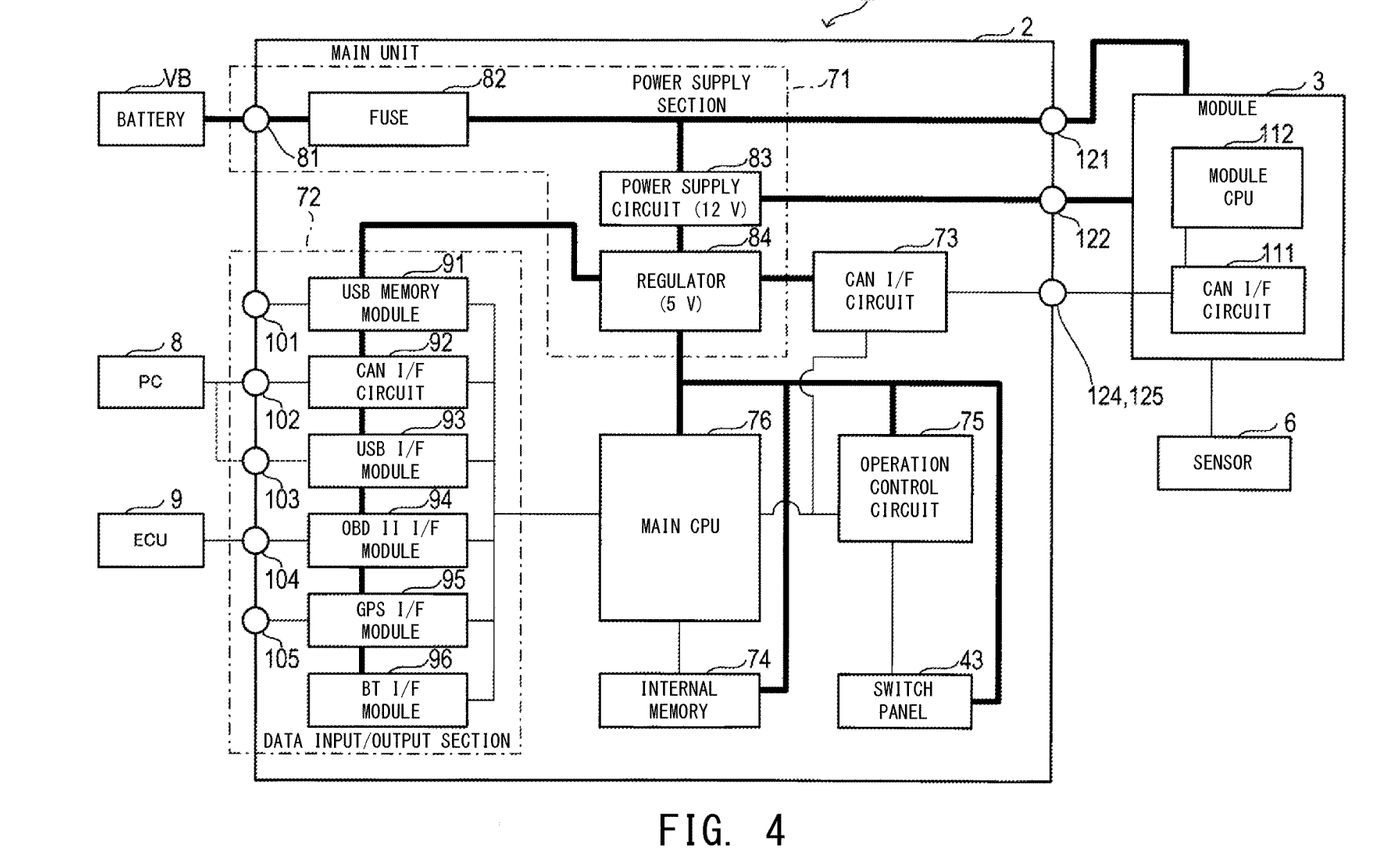
FIG. 4 is block diagram showing the configurations of the main unit 2 and the module 3.

As shown in FIG. 4, the main unit 2 includes a power supply section 71, a data input/output section 72, a CAN (Controller Area Network) interface circuit (hereinafter referred to as the CAN I/F circuit) 73, an internal memory 74, an operation control circuit 75, and a main CPU (Central Processing Unit) 76.

The power supply section 71 includes a power supply connector 81, a fuse 82, a power supply circuit 83, and a regulator 84.

The power supply connector 81 is a connector which is connected to a battery VB so as to receive a battery voltage from the battery VB.

The fuse 82 is provided in a power supply path between the power supply connector 81 and VB terminals 121 (see FIG. 5) of the module connection connectors 61 to 66. When an excessively large current flows through the power supply path, the fuse 82 is blown out.

The power supply circuit 83 receives the battery voltage from the battery VB through the fuse 82, generates a voltage of 12 V from the battery voltage, and outputs the generated voltage (12 V) through 12-V terminals 122 (see FIG. 5) of the module connection connectors 61 to 66.

The regulator 84 receives the 12 V voltage from the power supply circuit 83 and generates a voltage of 5 V. The regulator 84 outputs the generated voltage (5 V) to the data input/output section 72, the CAN I/F circuit 73, the internal memory 74, the operation control circuit 75, the main CPU 76, and the switch panel 43.

The data input/output section 72 includes a USB (Universal Serial Bus) memory module 91, a CAN I/F circuit 92, a USB interface module 93, an OBD (On Board Diagnosis) 2 interface module 94, a GPS (Global Positioning System) interface module 95, and a Bluetooth (registered trademark) interface module 96. Hereinafter, the USB interface module 93, the OBD2 interface module 94, the GPS interface module 95, and the Bluetooth interface module 96 will be referred to as the USB I/F module 93, the OBD2 I/F module 94, the GPS I/F module 95, and the BT I/F module 96, respectively.

The data input/output section 72 includes a USB memory connector 101, a CAN communication connector 102, a USB connector 103, an OBD2 connector 104, and a GPS connector 105.

In accordance with a scheme conforming to the USB standard, the USB memory module 91 sends data to and receives data from a USB memory connected through the USB memory connector 101.

In accordance with the CAN communication protocol, the CAN I/F circuit 92 sends data to and receives data from a device (for example, a personal computer 8) connected through the CAN communication connector 102.

In accordance with a scheme conforming to the USB standard, the USB I/F module 93 sends data to and receives data from a device connected through the USB connector 103.

In accordance with a scheme conforming to the OBD2 standard, the OBD2 I/F module 94 sends data to and receives data from a device (for example, an onboard ECU (Electronic Control Unit) 9) connected through the OBD2 connector 104.

The GPS I/F module 95 is an interface which allows a GPS receiver (not shown) for receiving satellite signals from GPS satellites to be connected to the main unit 2 through the GPS connector 105.

The BT I/F module 96 performs short distance communications in accordance with a scheme conforming to the Bluetooth standard.

In accordance with the CAN communication protocol, the CAN I/F circuit 73 sends data to and receives data from the modules 3 connected to CAN_H terminals 124 and CAN_L terminals 125 (see FIG. 5) of the module connection connectors 61 to 66.

The internal memory 74 is a storage device for storing various data.

The operation control circuit 75 outputs to the main CPU 76 input operation information for specifying an input operation performed by a user through the switches of the switch panel 43. Also, the operation control circuit 75 controls the operations of the LED lamps of the switch panel 43 on the basis of instructions from the main CPU 76.

The main CPU 76 executes various types of processing on the basis of inputs from the data input/output section 72, the CAN I/F circuit 73, the internal memory 74, and the operation control circuit 75 and controls the data input/output section 72, the CAN I/F circuit 73, the internal memory 74, and the operation control circuit 75.

For example, the main CPU 76 stores in the internal memory 74 the measurement data received from the modules 3 through the CAN I/F circuit 73.

Also, the main CPU 76 stores the measurement data received from the modules 3 in a USB memory connected to the USB memory module 91.

Also, the main CPU 76 outputs the measurement data received from the modules 3 to the personal computer 8 connected to the CAN I/F circuit 92 or the USB I/F module 93.

Also, the main CPU 76 stores in the internal memory 74 the data received from the on-board ECU 9 connected to the OBD2 I/F module 94.

Also, the main CPU 76 calculates the present position of the main unit 2 on the basis of the satellite signals received from the GPS receiver connected to the GPS connector 105, and stores the calculated present position in the internal memory 74.

Also, the main CPU 76 uses the BT I/F module 96 so as to send the measurement data received from the modules 3 by means of short distance wireless communication.

Also, when the main CPU 76 receives measurement setting information, which shows the measurement conditions under which each module 3 performs measurement, from the personal computer 8 connected to the CAN I/F circuit 92 or the USB I/F module 93, the main CPU 76 sends the measurement setting information to the module 3 through the CAN I/F circuit 73. As a result, in the module 3 having received the measurement setting information, the measurement conditions are changed such that the module 3 performs measurement under the measurement conditions indicated by the measurement setting information.

The module 3 includes a CAN I/F circuit 111 and a module CPU 112.

The CAN I/F circuit 111 sends data to and receives data from the main unit 2 in accordance with the CAN communication protocol.

The module CPU 112 executes various types of processing on the basis of inputs from the sensor 6 and the CAN I/F circuit 111 and controls the sensor 6 and the CAN I/F circuit 111.

Figure 5:
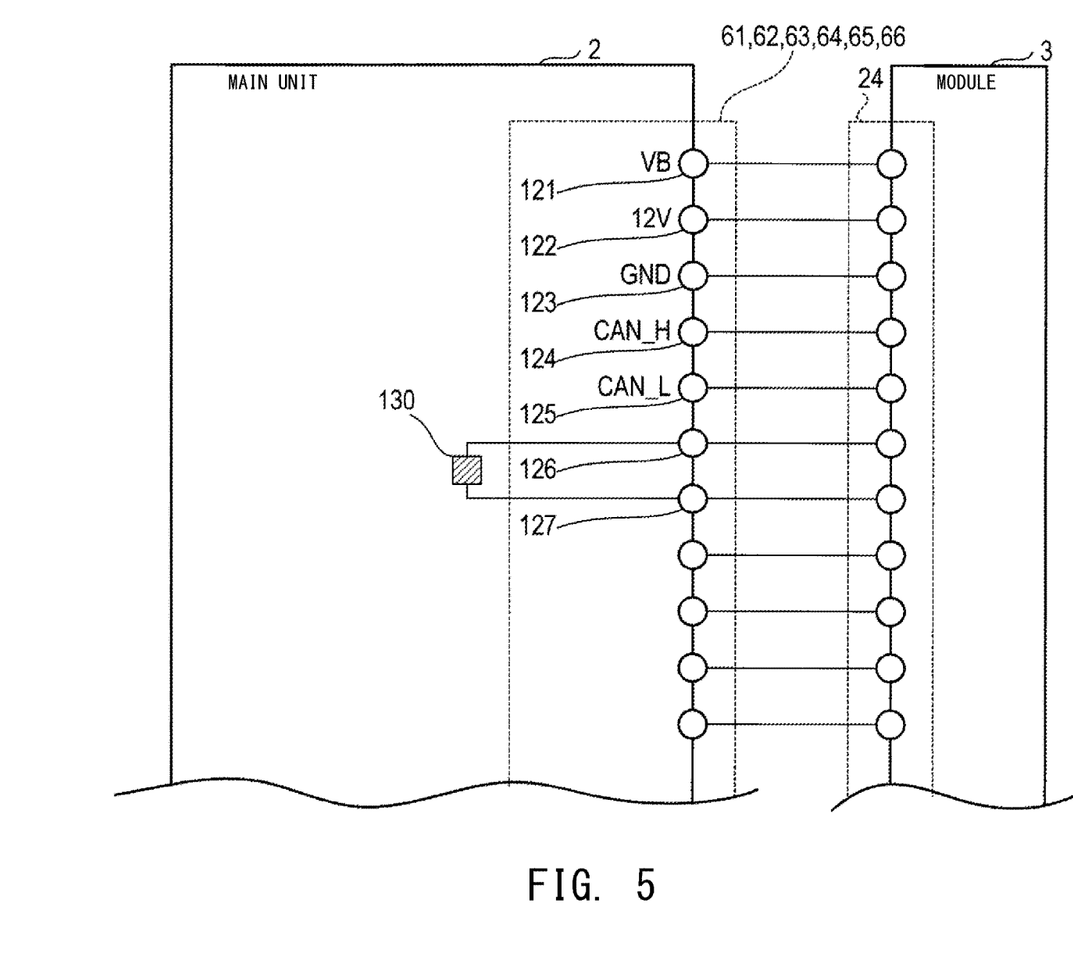
FIG. 5 is a diagram showing the configurations of a module connection connector 61-66 and a unit connection connector 24.

As shown in FIG. 5, each of the module connection connectors 61 to 66 of the main unit 2 has a plurality of terminals, including a VB terminal 121, a 12-V terminal 122, a GND terminal 123, a CAN_H terminal 124, a CAN_L terminal 125, and slot identification terminals 126, 127. The unit connection connector 24 of the module 3 has terminals corresponding to the plurality of terminals of the module connection connectors 61 to 66.

The VB terminal 121 is a terminal for supplying the battery voltage from the battery VB to the module 3. The 12-V terminal 122 is a terminal for supplying the 12 V voltage from the power supply circuit 83 to the module 3. The GND terminal 123 is a terminal for grounding the module 3. The CAN_H terminal 124 and the CAN_L terminal 125 are terminals for performing CAN communications between the main unit 2 and the module 3.

The slot identification terminals 126 and 127 are terminals for identifying the slot to which the module 3 is connected. One end and the other end of a slot identification resistor 130 are connected to the slot identification terminal 126 and the slot identification terminal 127.

Slot identification resistors 130 having different resistances are connected to the module connection connectors 61 to 66. In the present embodiment, slot identification resistors 130 whose resistances are 1 kΩ, 5 kΩ, 10 kΩ, 15 kΩ, 20 kΩ, and 25 kΩ, respectively, are connected to the module connection connectors 61, 62, 63, 64, 65, and 66.

Figure 6:
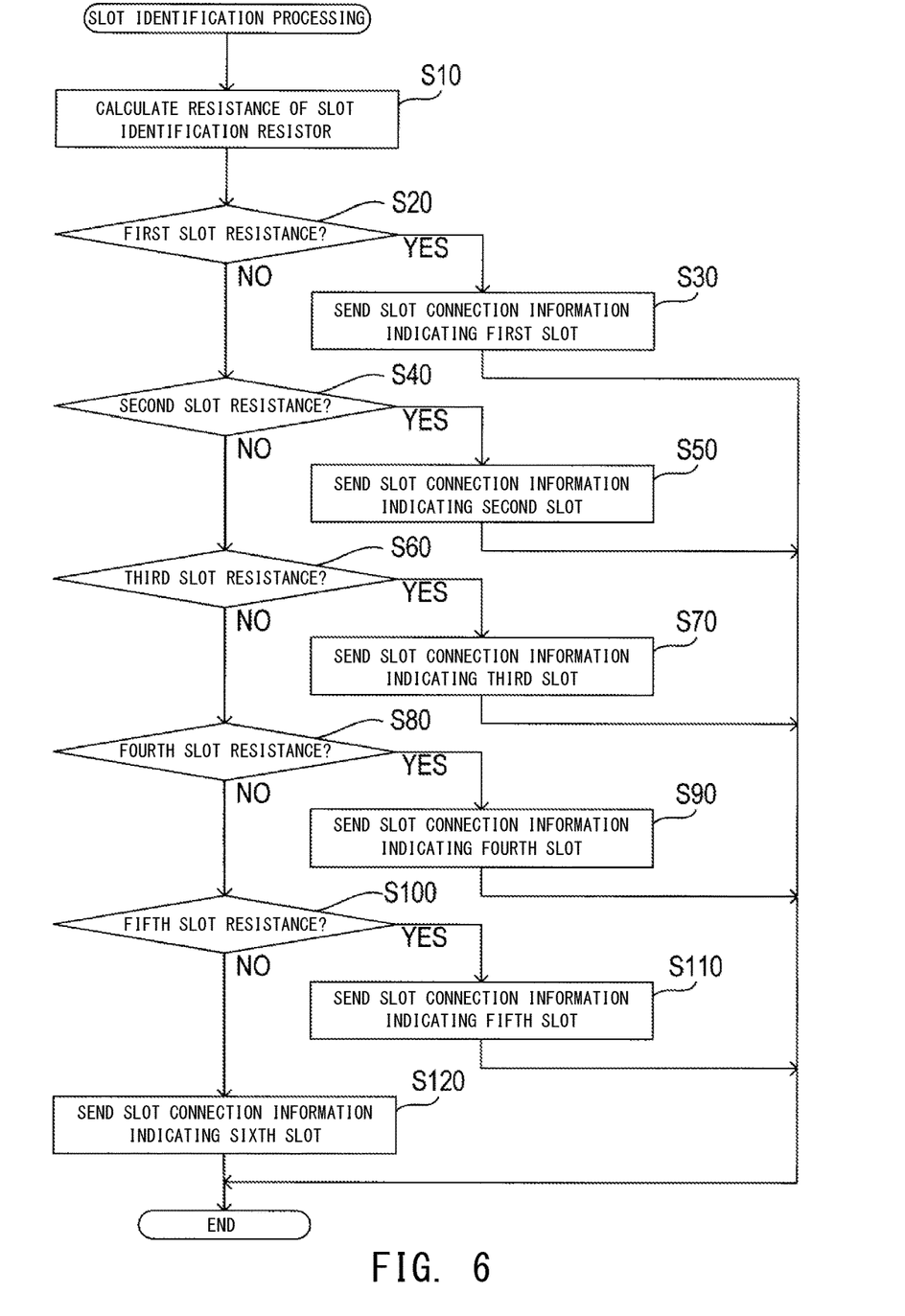
FIG. 6 is a flowchart showing slot identification processing.

Next, the steps of slot identification processing executed by the module CPU 112 of the module 3 will be described.

The slot identification processing is started after the module CPU 112 starts upon supply of voltage from the VB terminal 121 or the 12-V terminal 122 of the module 3.

When the slot identification processing is started, as shown in FIG. 6, the module CPU 112 first calculates the resistance of the slot identification resistor 130 in S10 by supplying a current having a predetermined identification current value between the terminals of the unit connection connector 24 corresponding to the slot identification terminals 126 and 127 and measuring the voltage between the two terminals.

In S20, the module CPU 112 judges whether or not the resistance calculated in S10 coincides with a first slot resistance (1 kΩ in the present embodiment) set in advance. In the case where the calculated resistance coincides with the first slot resistance (S20: YES), in S30, the module CPU 112 sends slot connection information to the main unit 2 by means of CAN communications. The slot connection information indicates that the module 3 is connected to the first slot. Subsequently, the module CPU 112 ends the slot identification processing.

Meanwhile, in the case where the calculated resistance does not coincide with the first slot resistance (S20: NO), in S40, the module CPU 112 judges whether or not the resistance calculated in S10 coincides with a second slot resistance (5 kΩ in the present embodiment) set in advance. In the case where the calculated resistance coincides with the second slot resistance (S40: YES), in S50, the module CPU 112 sends slot connection information to the main unit 2 by means of CAN communications. The slot connection information indicates that the module 3 is connected to the second slot. Subsequently, the module CPU 112 ends the slot identification processing.

Meanwhile, in the case where the calculated resistance does not coincide with the second slot resistance (S40: NO), in S60, the module CPU 112 judges whether or not the resistance calculated in S10 coincides with a third slot resistance (10 kΩ in the present embodiment) set in advance. In the case where the calculated resistance coincides with the third slot resistance (S60: YES), in S70, the module CPU 112 sends slot connection information to the main unit 2 by means of CAN communications. The slot connection information indicates that the module 3 is connected to the third slot. Subsequently, the module CPU 112 ends the slot identification processing.

Meanwhile, in the case where the calculated resistance does not coincide with the third slot resistance (S60: NO), in S80, the module CPU 112 judges whether or not the resistance calculated in S10 coincides with a fourth slot resistance (15 kΩ in the present embodiment) set in advance. In the case where the calculated resistance coincides with the fourth slot resistance (S80: YES), in S90, the module CPU 112 sends slot connection information to the main unit 2 by means of CAN communications. The slot connection information indicates that the module 3 is connected to the fourth slot. Subsequently, the module CPU 112 ends the slot identification processing.

Meanwhile, in the case where the calculated resistance does not coincide with the fourth slot resistance (S80: NO), in S100, the module CPU 112 judges whether or not the resistance calculated in S10 coincides with a fifth slot resistance (20 kΩ in the present embodiment) set in advance. In the case where the calculated resistance coincides with the fifth slot resistance (S100: YES), in S110, the module CPU 112 sends slot connection information to the main unit 2 by means of CAN communications. The slot connection information indicates that the module 3 is connected to the fifth slot. Subsequently, the module CPU 112 ends the slot identification processing.

Meanwhile, in the case where the calculated resistance does not coincide with the fifth slot resistance (S100: NO), in S120, the module CPU 112 sends slot connection information to the main unit 2 by means of CAN communications. The slot connection information indicates that the module 3 is connected to the sixth slot. Subsequently, the module CPU 112 ends the slot identification processing.

The measurement apparatus 1 configured as described above includes the modules 3a, 3b, 3c, and 3d and the main unit 2 which collects measurement data output from the module 3a, 3b, 3c, and 3d.

The housing 11 of the main unit 2 can be carried by a user of the measurement apparatus 1, and the modules 3a, 3b, 3c, and 3d are removably accommodated in the housing 11. The CAN I/F circuit 73 collets measurement data output from the modules 3 accommodated in the housing 11.

The main CPU 76 outputs the collected measurement data to the personal computer 8 or the like. The internal memory 74 and the USB memory connected to the USB memory module 91 store the collected measurement data.

As described above, after the modules 3 are installed into the housing 11, the measurement apparatus 1 collects measurement data from the modules 3. The measurement apparatus 1 performs at least one of an operation of outputting the collected measurement data to the personal computer 8 or the like and an operation of storing the collected data in the internal memory 74 or the like. As a result, the measurement apparatus 1 allows the measurement data from the modules 3 to be utilized at the personal computer 8 or to be obtained from the internal memory 74 or the like and be utilized.

The measurement apparatus 1 is configured such that a plurality of modules 3 can be removably accommodated in the housing 11. Therefore, the measurement apparatus 1 allows a user to install a module 3 having a desired measurement function in the housing 11, whereby the user can collect desired measurement data. Thus, the convenience of the measurement apparatus 1 can be improved.

In the measurement apparatus 1, when a trouble occurs in a module 3 installed in the housing 11, the module 3 having a trouble can be removed from the housing 11. Therefore, in the measurement apparatus 1, when a trouble occurs in a module 3, the trouble can be solved without replacing the entire measurement apparatus 1. Thus, the convenience of the measurement apparatus 1 can be improved.

Further, since the measurement apparatus 1 is configured such that the housing 11 for accommodating the modules 3 can be carried, the degree of freedom of the installation location of the measurement apparatus 1 can be increased.

Also, the measurement apparatus 1 has the module connection connectors 61, 62, 63, 64, 65, and 66 which are disposed within the housing 11 and which are detachably connected to the modules 3. The module connection connectors 61 to 66 have the same shape and are disposed along the slot arrangement direction Ds set in advance. As a result, the measurement apparatus 1 allows a plurality of modules 3 having the same measurement function to be attached to the main unit 2 of the measurement apparatus 1. Further, the unit connection connectors 24 attached to the modules 3a, 3b, 3c, and 3d have the same shape. Therefore, each of the modules 3a, 3b, 3c, and 3d can be attached to any of the module connection connectors 61 to 66 disposed within the housing 11. As a result, the measurement apparatus 1 can increase the degree of freedom of the installation position of each module 3 within the housing 11.

Also, in the measurement apparatus 1, the module connection connectors 61 to 66 are disposed at intervals equal to the slot width Ws along the slot arrangement direction Ds. The slot width Ws is set such that it corresponds to the length of the modules 3b, 3c, and 3d along the slot arrangement direction Ds. Notably, the modules 3b, 3c, and 3d are modules whose length along the slot arrangement direction Ds is the smallest among the modules 3a, 3b, 3c, and 3d.

As a result, the measurement apparatus 1 allows a plurality of modules 3 to be attached to the main body portion along the slot arrangement direction Ds at intervals equal to n times the slot width Ws, where n is an integer. Therefore, the measurement apparatus 1 allows the length of each module 3 along the slot arrangement direction Ds to be freely set in accordance with the capacity of the housing 11; i.e., the number of modules 3 which can be accommodated in the housing 11.

Also, in the measurement apparatus 1, the module CPU 112 of each module 3 detects one of the module connection connectors 61 to 66 which is connected to the module 3. As a result, the measurement apparatus 1 can specify the location (namely, the slot) of each module 3 accommodated in the housing 11, the location being that within the housing 11.

Also, in the measurement apparatus 1, each of the modules 3b, 3c, and 3d uses a direct-insertion-type sensor as the sensor 6. As a result, the measurement apparatus 1 can detect the state of exhaust gas without introducing the exhaust gas into the modules 3b, 3c, and 3d.

Also, in the measurement apparatus 1, each sensor 6 and the corresponding module 3 are detachably connected together. As a result, in the measurement apparatus 1, when a trouble occurs in the sensor 6, the trouble can be solved by replacing the sensor 6 only without replacing both the sensor 6 and the module 3. Thus, the convenience of the measurement apparatus 1 can be improved.

In the measurement apparatus 1, the main unit 2 and the modules 3 can send and receive data therebetween. As a result, the measurement apparatus 1 can not only collect measurement data from the modules 3 but also provide information to the modules 3.

Also, in the measurement apparatus 1, the GPS I/F module 95 obtains information for specifying the present position of the measurement apparatus 1. As a result, the measurement apparatus 1 can relate the present position of the measurement apparatus 1 to the measurement results of the modules 3.

In the above-described embodiment, the main unit 2 is the main body portion in the present invention, the modules 3 are the measurement modules in the present invention, the CAN I/F circuit 73 is the data collection unit in the present invention, the main CPU 76 is the output unit in the present invention, the internal memory 74 and the USB memory connected to the USB memory module 91 are the storage section of the present invention, and the personal computer 8 is the output destination device in the present invention.

Also, the module connection connectors 61 to 66 are the connection connectors in the present invention, the module CPU 112 is the connection detection unit in the present invention, and the GPS I/F module 95 is the position information obtainment unit in the present invention.

Also, the modules 3b, 3c, and 3d are the measurement module having the shortest length in the present invention, and the slot width Ws is the shortest arrangement direction length in the present invention.

Although one embodiment of the present invention has been described, the present invention is not limited to the above-described embodiment, and the present invention can be implemented in various forms without departing from the technical scope of the present invention.

For example, in the above-described embodiment, the amount of particulate matters contained in exhaust gas discharged from a diesel engine, the concentration of nitrogen oxides contained in the exhaust gas, etc. are measured. However, the physical quantities measured by the modules 3 are not limited thereto.

In the above-described embodiment, the modules 3 are accommodated while being lined up along a horizontal direction. However, the the modules 3 may be accommodated while being lined up along a vertical direction, or may be accommodated while being lined in two or more rows along a horizontal or vertical direction.

In the above-described embodiment, the measurement data received from the modules 3 are stored in the internal memory 74. However, in the case where the main unit 2 has a display unit, the measurement results represented by the measurement data received from the modules 3 may be displayed on the display unit.

DESCRIPTION OF REFERENCE NUMERALS

1: measurement apparatus, 2: main unit, 3: module, 6: sensor, 8: personal computer, 11: housing, 12: handle, 61 to 66: module connection connector, 72: data input/output section, 73: CAN I/F circuit, 74: internal memory, 76: main CPU, 111: CAN I/F circuit, 112: module CPU

The invention claimed is:

1. A measurement apparatus comprising:
    a plurality of measurement modules which are connected to sensors in one-to-one relation and each of which includes at least a circuit configured to receive a sensor output from the corresponding sensor and to output the received sensor output; and
    a main body portion which collects data output from the measurement modules,
    wherein the main body portion includes:
        a housing which can be carried by a user of the measurement apparatus and in which the plurality of measurement modules are removably accommodated;
        a data collection unit that collects the data output from the measurement modules;
        at least one output unit that outputs the collected data to an output destination device set in advance and a storage section where the data is stored;
        a physical quantity detected by each of the sensors corresponds to a function of each of the measurement modules;
        a plurality of connectors which are disposed within the housing and which are detachably connected to the measurement modules; and
        a plurality of slot identification resistors that are connected to the plurality of connectors,
    wherein the plurality of connectors have the same shape and are arranged along an arrangement direction set in advance, and each measurement module includes a connection detection unit that detects one of the plurality of connectors based on a resistance of a respective one of each of the slot identification resistors.

2. The measurement apparatus according to claim 1, wherein
    the measurement module having the shortest length along the arrangement direction among the plurality of measurement modules is defined as a smallest measurement module, and
    the plurality of connectors are arranged along the arrangement direction at intervals equal to a shortest arrangement direction length set in advance to coincide with the length of the smallest measurement module along the arrangement direction.

3. The measurement apparatus according to claim 1, wherein at least one of the plurality of measurement modules uses a direct-insertion-type sensor which is directly inserted into an exhaust pipe of an internal combustion engine so as to detect a state of exhaust gas within the exhaust pipe.

4. The measurement apparatus according to claim 1, wherein each sensor and the corresponding measurement module are detachably connected together.

5. The measurement apparatus according to claim 1, wherein the main body portion and the measurement modules can send and receive data therebetween.

6. The measurement apparatus according to claim 1, further comprising a position information obtainment unit that obtains information for specifying a present position of the measurement apparatus.

7. The measurement apparatus according to claim 1, wherein
the plurality of measurement modules are connected to sensors via sensor connection ports, and
at least one of the measurement modules consists of a single sensor connection port.

8. The measurement apparatus according to claim 1, wherein each of the plurality of slot identification resistors has a different resistance and is connected to a different connector.

9. The measurement apparatus according to claim 1, wherein
the plurality of slot identification resistors are connected to a plurality of slot identification terminals, each of which being configured to identify a slot to which the measurement module is connected.

10. The measurement apparatus according to claim 1, wherein the housing contains six slot identification resistors having resistances of 1 k$\Omega$, 5 k$\Omega$, 10 k$\Omega$, 15 k$\Omega$, 20 k$\Omega$, and 25 k$\Omega$, respectively.

11. The measurement apparatus according to claim 9, wherein each of the plurality of measurement modules has a unit connection connector with plural terminals and is configured to calculate the resistance of each of the slot identification resistors by supplying a current having a predetermined identification current value between the terminals of the unit connection connector corresponding to the slot identification terminals.

* * * * *